(12) United States Patent
Maeda et al.

(10) Patent No.: US 6,433,339 B1
(45) Date of Patent: Aug. 13, 2002

(54) SURFACE STATE MONITORING METHOD AND APPARATUS

(75) Inventors: Yasuhiro Maeda; Haruo Yoshida; Michiaki Endo, all of Tokyo (JP)

(73) Assignee: Advantest Corp., Tokyo (JP)

( * ) Notice: Subject to any disclaimer, the term of this patent is extended or adjusted under 35 U.S.C. 154(b) by 38 days.

(21) Appl. No.: 09/676,593

(22) Filed: Sep. 29, 2000

(30) Foreign Application Priority Data

Sep. 30, 1999 (JP) .......................................... 11-278759

(51) Int. Cl.[7] .................................................. G01J 3/42
(52) U.S. Cl. ................... 250/341.4; 356/237.4; 356/237.5; 438/16
(58) Field of Search .................... 250/341.4; 438/16; 356/237.4, 237.5; 414/331.15, 331.14, 935, 416.08

(56) References Cited

U.S. PATENT DOCUMENTS

| | | | |
|---|---|---|---|
| 4,895,486 A | * | 1/1990 | Baker et al. ................ 414/331 |
| 5,321,264 A | * | 6/1994 | Kuwabara et al. ...... 250/339.01 |
| 5,381,234 A | * | 1/1995 | Barbee et al. .............. 356/369 |

* cited by examiner

Primary Examiner—Seungsook Ham
Assistant Examiner—Timothy Moran
(74) Attorney, Agent, or Firm—Muramatsu & Associates

(57) ABSTRACT

The surface state monitoring apparatus comprises: a wafer cassette holding a plurality of semiconductor wafers; an incidence optical system for applying infrared radiation to at least one of said plurality of semiconductor wafers; a detection optical system for detecting the infrared radiation which has undergone multiple reflection in the semiconductor wafer and exited from the semiconductor wafer; surface state monitoring means for monitoring surface states of the semiconductor wafer, based on the infrared radiation detected by the detection optical system; and displacing means for displacing the wafer cassette relative to the incidence optical system and the detection optical system. Surface states of said plurality of semiconductor wafers are sequentially monitored while the wafer cassette is displaced relative to the incidence optical system and the detection optical system by the displacing means, whereby surface states of said plurality of semiconductor wafers held in the wafer cassette are continuously monitored.

15 Claims, 13 Drawing Sheets

| POINT | x | y |
|-------|---|---|
| A | 75 μm | 0 μm |
| B | 500 μm | 0 μm |
| C | 50 μm | 258 μm |
| D | 0 μm | 75 μm |

SURFACE STATE MONITORING METHOD AND APPARATUS

BACKGROUND OF THE INVENTION

The present invention relates to a surface state monitoring method and apparatus for monitoring surface states of semiconductor wafers, more specifically a surface state monitoring method and apparatus which can monitor surface states of a plurality of semiconductor wafers continuously for a short period of time.

Various requirements at fabrication sites of semiconductor devices require surface states of the semiconductor substrates being accurately grasped.

In the field of semiconductor integrated circuits of memory devices, such as DRAM (Dynamic Random Access Memory), etc., and of logic devices, as a device has higher integration, the gate insulation film at the time of the fabrication of the device is made thinner, and the device has a design that the function for insulating an electric field (about $4 \times 10^6$ V/cm) of a MOS (Metal Oxide Semiconductor) FET (Field Effect Transistor) in operation has a small margin. Generally, a gate insulation film is formed by thermal oxidation. In forming a gate insulation film by thermal oxidation, in a case of surface contamination, as of metal contamination, chemical contamination, organic contamination or others is present, there is a risk that dielectric breakdown of the formed gate insulation film may be induced. It is known that organic contaminants stayed on the substrate surfaces after the gate insulation film has been formed results in insulation deterioration. Thus, it is very important to form a gate insulation film having dielectric breakdown voltage of a required value that surface states of a semiconductor substrate are administered.

Plasma etching is widely used in steps of patterning device structures. The plasma etching process is determined by dynamic balance in adsorption, reaction and elimination processes between influxes of radical ions, etc. fed in gas phase and outfluxes from semiconductor wafer surfaces. Thus, in the plasma etching process, to set optimum plasma etching conditions and to detect the end point of the plasma etching, it is very effective to know adsorption states, chemical bonding states, structures and thicknesses of reaction layers, etc. of surface states of semiconductor wafers.

Recently, semiconductor devices have elements increasingly micronized, and are made increasingly three dimensional. This makes it difficult for cleaning solutions to intrude into micronized regions or steep steps or to be replaced there. In consideration of future further micronization, dry cleaning is noted. For example, to remove organic contaminants staying on silicon wafers reaction with ozone or oxygen excited by UV radiation is effective. Oxygen molecules are dissolved to oxygen atoms by light of a below 242 nm wavelength. The organic contaminants are oxidized by the oxygen atoms and solved into $H_2O$, $O_2$, CO, $CO_2$, etc. of high vapor pressures. Organic bonds, such as C—C, C—H, C—O, etc. can be dissolved by UV radiation. Thus, knowing surface states of semiconductor wafers is very important also to control parameters for the dry cleaning, such as an optimum amount of radiation, wavelength, oxygen amount, etc.

Native oxide films formed on the surfaces of silicon wafers are not usable in devices because their thickness cannot be controlled. Accordingly, it is preferable that when a device is fabricated on a silicon wafer, native oxide film on the silicon substrate is removed, and silicon bonds on the surfaces are terminated with hydrogen to stabilize the surfaces of the silicon wafer. This is because hydrogen can be eliminated at a relatively low temperature of about 500° C., and the termination with hydrogen relatively little affects the following processes. Most of silicon atoms on the surfaces of a silicon wafer subjected to UV ozone cleaning and hydrogen fluoride etching are terminated with hydrogen, and Si=$H_2$ and Si—H are formed. Accordingly, if a state of the-termination with hydrogen on silicon wafer surfaces, temperature dependency of the elimination of terminating hydrogen can be monitored, the silicon wafer surfaces at the start of semiconductor processing can be kept in a suitable state. Higher quality and higher yields can be expected.

Thus, it is very important to know a surface state of a semiconductor wafer in a fabrication process of a semiconductor device, and various monitoring methods and apparatuses have been proposed and locally practiced.

Means for monitoring a surface state of a semiconductor wafer by internal multiple reflection of infrared radiation is provided by, e.g., FT-IR (Fourier-transform spectroscopy) apparatus or the special use marketed by Perkin-Elmer Co., U.S.A. For wider applications of the means Graseby Specac Limited, for example, markets various accessories.

In the conventional surface state monitoring method using this means, as exemplified in FIG. 13A, a substrate-to-be-monitored 102 is cut into, e.g., a 40 mm×10 mm strip, and infrared radiation emitted from an infrared radiation source 104 is passed through the substrate-to-be-monitored 102 to monitor states of the substrate surfaces. Otherwise, as exemplified in FIG. 13B, a substrate-to-be-monitored 102 has the end tapered, and infrared radiation is incident on the end surface of the substrate-to-be-monitored 102 to undergo multiple reflection inside the substrate, whereby a surface state of the substrate is monitored. Otherwise, as exemplified in FIG. 13C, infrared radiation is incident on a substrate-to-be-monitored via a prism 106 positioned above the substrate to undergo multiple reflection inside the substrate, whereby a surface state of the substrate is monitored.

The basic principle of monitoring a surface state of a substrate by applying infrared radiation to a substrate to cause the infrared radiation to undergo internal multiple reflection is as follows. When the frequency of an evanescent wave oozing when the infrared radiation reflects on the surface of the substrate agrees with the molecular vibrational frequency of the organic contaminants on the substrate surface, the specific frequency component of the infrared radiation is resonance-absorbed. Thus, kinds and amounts of the organic contaminants can be determined by measuring the spectra of the infrared radiation. The basic principle also has a function that information of organic contaminants on substrate surfaces is gradually made more exact. A signal vs. noise ratio (S/N ratio) is also improved.

However, these monitoring methods needs cutting a substrate-to-be-monitored into strips, additionally machining a substrate-to-be-monitored, or disposing a prism above a substrate-to-be-monitored. These monitoring methods have not been usable in the in-situ monitoring at site of fabricating semiconductor devices.

Methods of monitoring organic contaminants on semiconductor substrates are known thermal desorption GC/MS (Gas Chromatography/Mass Spectroscopy), APIMS (Atmospheric Pressure Ionization Mass Spectroscopy), TDS (Thermal Desorption Spectroscopy), etc. However, these methods are not suitable to be used in in-situ monitoring at site of fabricating semiconductors for reasons that these methods cannot directly observe large wafers of, e.g., above 300 mm-diameters which are expected to be developed, and need vacuum ambient atmosphere, and have low throughputs, and other reasons.

As described above, the above-described conventional surface state monitoring methods are not usable in the in-situ monitoring at site of fabricating semiconductor devices because the monitoring by these method is destructive, or these methods are not suitable for monitoring large semiconductor wafers. Surface state monitoring methods and apparatuses which permit the in-situ monitoring of substrate surfaces at site of fabricating semiconductor devices, and permit large wafers to be monitored have been expected.

In view of the above, the inventors of the present application have already proposed an organic contaminant detecting method using wafer internal multiple reflection Fourier transformation infrared spectroscopy (see, e.g., the specification of Japanese Patent Application No. 95853/1999). When infrared radiation is applied to one end of a wafer at a specific incidence angle, the infrared radiation propagates inside the wafer, repeating total reflections on both surfaces. The infrared radiation oozes the surfaces of the wafer (evanescent waves), and a part of infrared spectra is absorbed by organic contaminants staying on the surfaces. The propagated infrared radiation emitted at the other end of the wafer is spectroscopically analyzed by FT-IR to thereby detect and identify the organic contaminants staying on the surfaces of the wafer. This monitoring method has sensitivity equal to GC/MS, and in addition thereto the monitoring has realtime, and simple and economical.

In the surface state monitoring method described in the specification of Japanese Patent Application No. 95853/1999, the offset shape of a wafer is used to induce infrared radiation into the wafer at the declined part of the peripheral edge of the wafer. Accordingly, it is not necessary to machine the semiconductor wafer itself, which permits the in-situ monitoring in the process for fabricating a semiconductor device.

However, in the respective fabrication steps of a semiconductor device mass-production line, the process is generally conducted by a single wafer processing. Thus, it takes time to monitor a plurality of wafers sequentially wafer by wafer in the wafer monitor following the processing, which affects throughput of the fabrication steps as a whole. To administer production throughput per rot, monitor results or statistic monitoring per rot is necessary. Also to this end, it is a significant problem that the monitor of each wafer takes less time.

SUMMARY OF THE INVENTION

An object of the present invention is to provide a surface state monitoring method and apparatus which can monitor a plurality of wafers continuously and for a short period of time.

The above-described object is achieved by a surface state monitoring apparatus comprising: a wafer cassette holding a plurality of semiconductor wafers; an incidence optical system for applying infrared radiation to at least one of said plurality of semiconductor wafers; a detection optical system for detecting infrared radiation which has undergone multiple reflection in the semiconductor wafer and exited from the semiconductor wafer; surface state monitoring means for monitoring surface states of the semiconductor wafer, based on the infrared radiation detected by the detection optical system; and displacing means for displacing the wafer cassette relative to the incidence optical system and the detection optical system, surface states of said plurality of semiconductor wafers being sequentially monitored while the wafer cassette is displaced relative to the incidence optical system and the detection optical system by the displacing means, whereby surface states of said plurality of semiconductor wafers held in the wafer cassette are continuously monitored.

The above-described object is achieved by a surface state monitoring apparatus comprising: a wafer cassette holding a plurality of semiconductor wafers; an incidence optical system for applying infrared radiation to at least one of said plurality of semiconductor wafers; a detection optical system for detecting infrared radiation which has undergone multiple reflection in the semiconductor wafer and exited from the semiconductor wafer; and surface state monitoring means for monitoring surface states of the semiconductor wafer, based on the infrared radiation detected by the detection optical system, the incidence optical system being controlled to apply the infrared radiation sequentially to said semiconductor wafers, whereby surface states of said plurality of semiconductor wafers held in the wafer cassette being continuously monitored.

The above-described object is achieved by a surface state monitoring apparatus comprising: a wafer cassette holding a plurality of semiconductor wafers; an incidence optical system for applying infrared radiation to at least two or more of said semiconductor wafers; a detection optical system for collectively detecting infrared radiations which have undergone multiple reflection in the semiconductor wafers and exited from the semiconductor wafers, respectively; and surface state monitoring means for monitoring surface states of the semiconductor wafers, based on the infrared radiations detected by the detection optical system.

In the above-described surface state monitoring apparatuses, it is possible that the apparatus further comprises: displacing means for displacing the wafer cassette relative to the incidence optical system and the detection optical system.

The above-described object is achieved by a surface state monitoring method comprising: applying infrared radiation to at least one of a plurality of semiconductor wafers held in a wafer cassette, detecting infrared radiation which has undergone multiple reflection in the semiconductor wafer and exited from the semiconductor wafer, and analyzing the detected infrared radiation to monitor surface states of the semiconductor wafer, surface states of the semiconductor wafer being monitored while the wafer cassette is displaced relative to an infrared radiation optical system to continuously monitor surface states of said plurality of semiconductor wafers held in the wafer cassette.

In the above-described surface state monitoring method, it is possible that the wafer cassette is intermittent displaced wafer by wafer relative to the infrared radiation optical system.

In the above-described surface state monitoring method, it is possible that the wafer cassette is continuously displaced relative to the infrared radiation optical system.

In the above-described surface state monitoring method, it is possible that a displacement of the wafer cassette relative to the infrared radiation optical system, and a monitor of surface states of the semiconductor wafer are synchronized with each other.

The above-described object is achieved by a surface state monitoring method comprising: applying infrared radiation to at least one of a plurality of semiconductor wafers held in a wafer cassette, detecting infrared radiation which has undergone multiple reflection in the semiconductor wafer and exited from the semiconductor wafer, and analyzing the detected infrared radiation to monitor surface states of the semiconductor wafer, an infrared radiation optical system being controlled to apply infrared radiation sequentially to a different one of said plurality of semiconductor wafers, whereby surface states of said plurality of semiconductor wafers held in the wafer cassette are continuously monitored.

In the above-described surface state monitoring method, it is possible that a control of the infrared radiation optical system and a monitor of surface states of the semiconductor wafer are synchronized with each other.

The above-described object is achieved by a surface state monitoring method comprising: applying infrared radiation to respective at least two or more of a plurality of semiconductor wafers held in a wafer cassette; collectively detecting infrared radiations which has undergone multiple reflection in the semiconductor wafers and exited from the semiconductor wafers, respectively; and analyzing the detected infrared radiation to monitor surface states of the semiconductor wafers.

In the above-described surface state monitoring method, it is possible that surface states of said plurality of semiconductor wafers held in the wafer cassette are collectively monitored.

According to the present invention, surface states of semiconductor wafers can be discontiguously and non-destructively monitored continuously and for a short period of time, held in wafer cassettes. Means for storing monitored data for each wafer is provided, whereby wafers can be monitored not only sheet by sheet but also in the unit of a wafer cassette. The monitored data can be utilized for statistic administration of fabrication yields.

DETAILED DESCRIPTION OF THE INVENTION

A First Embodiment

The surface state monitoring method and apparatus according to a first embodiment of the present invention will be explained with reference to FIGS. 1, 2, 3A–3B, 4A–4B, and 5–7.

Figure 1:
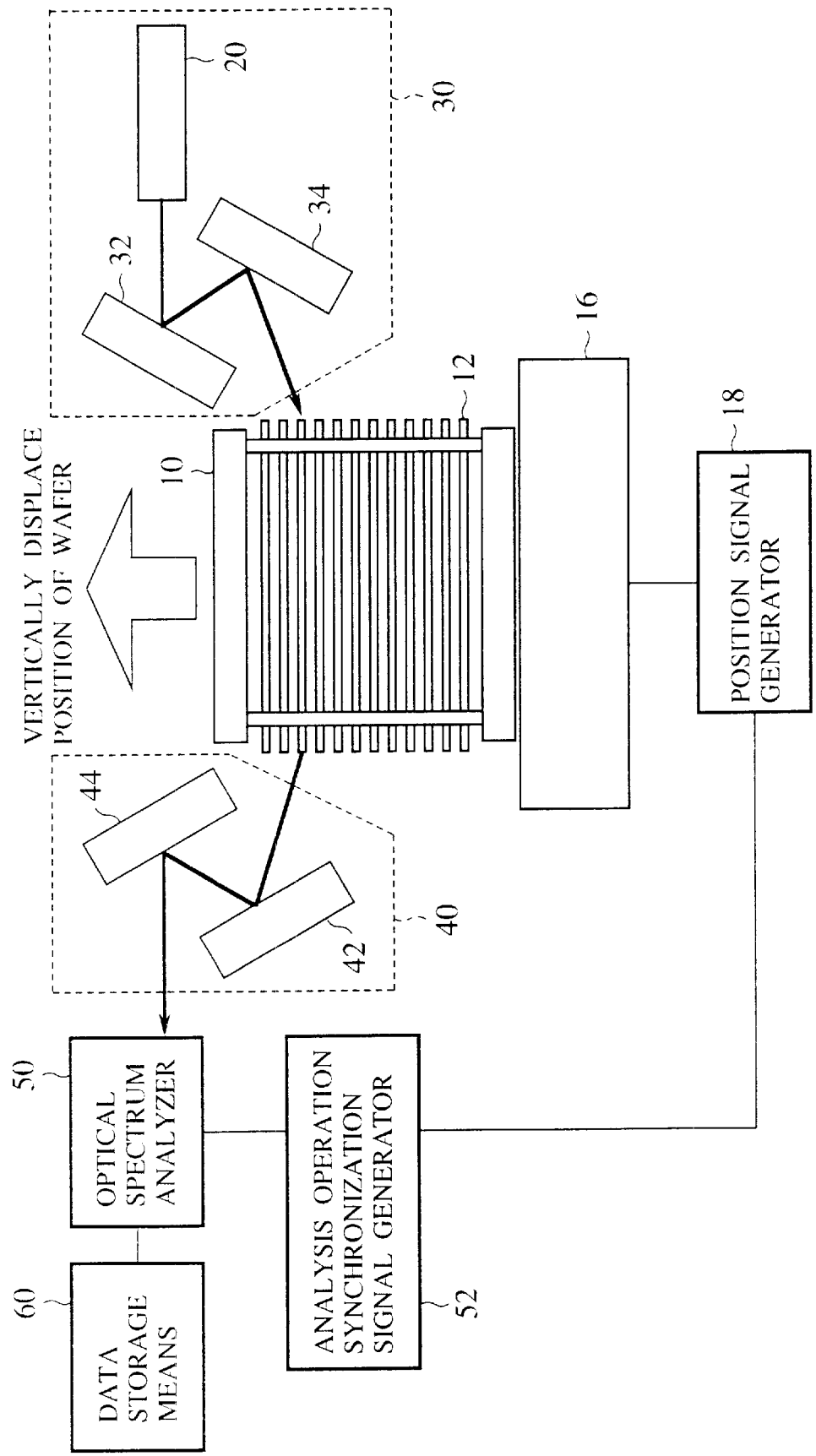
FIG. 1 is a diagrammatic view of the surface state monitoring apparatus according to a first embodiment of the present invention.
Figure 2:
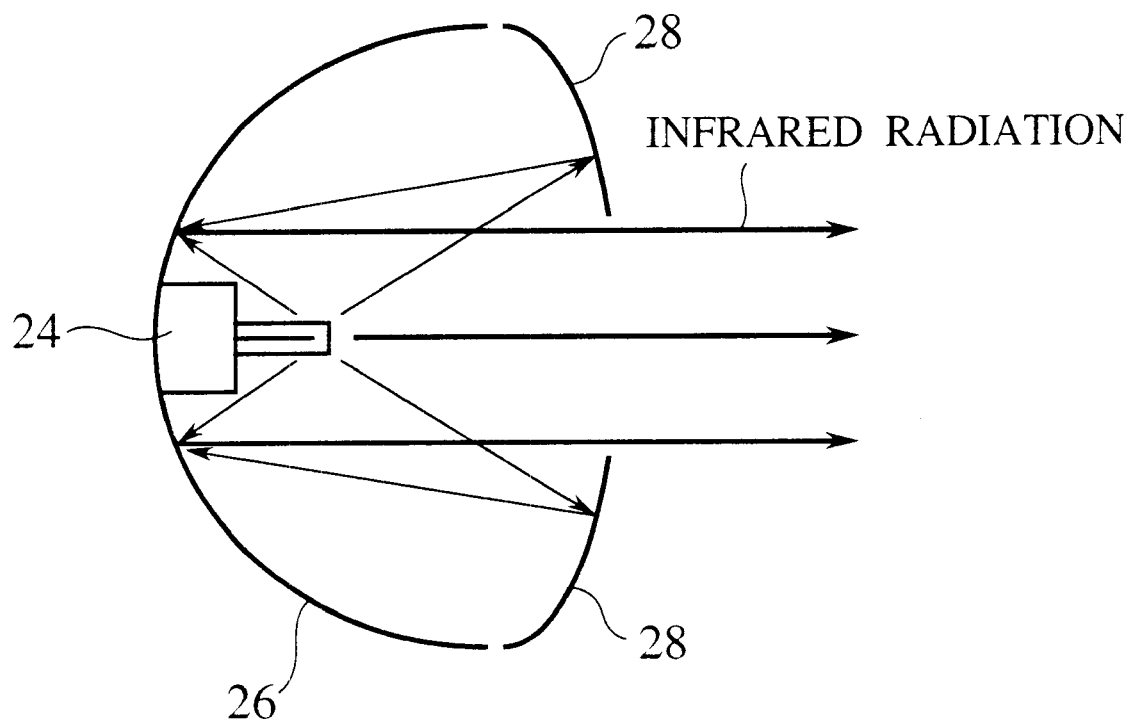
FIG. 2 is a diagrammatic sectional view of an infrared radiation source of the surface state monitoring apparatus according to the first embodiment of the present invention.
Figure 3A:
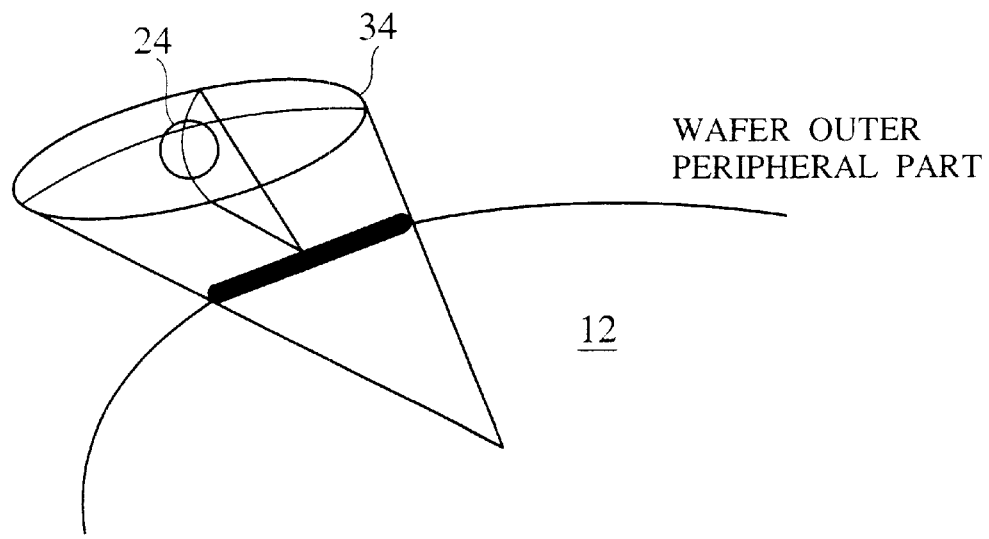
FIGS. 3A and 3B are views explaining a method for condensing by a concave mirror infrared radiation along the wafer outer peripheral part.
Figure 3B:
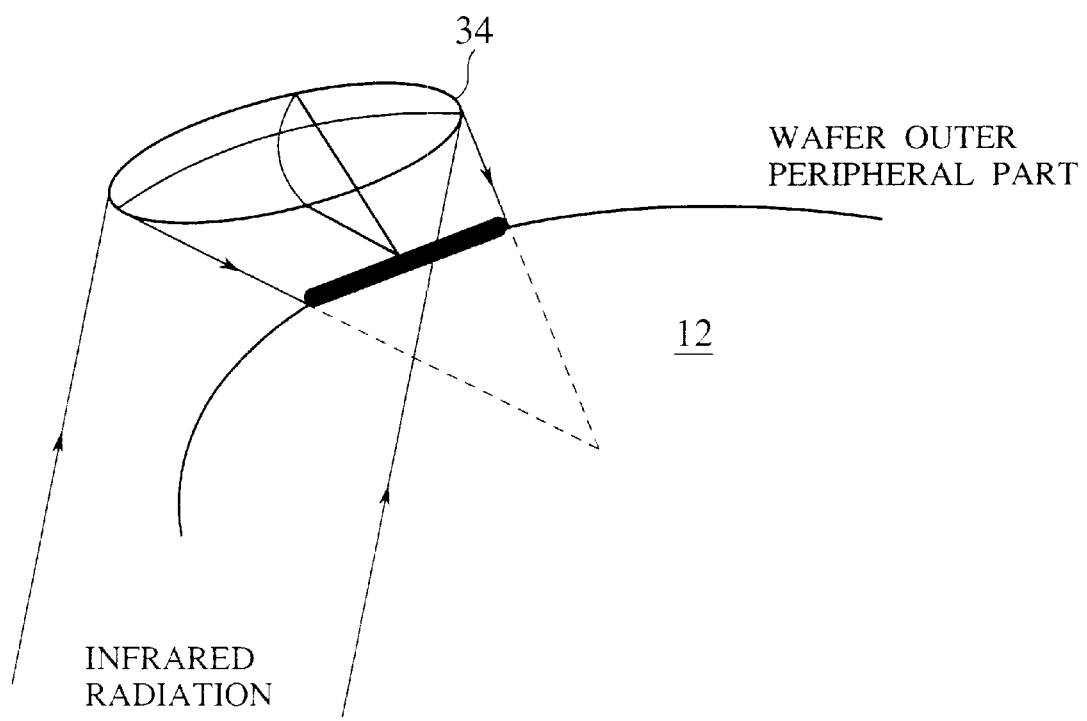
Figure 4A:
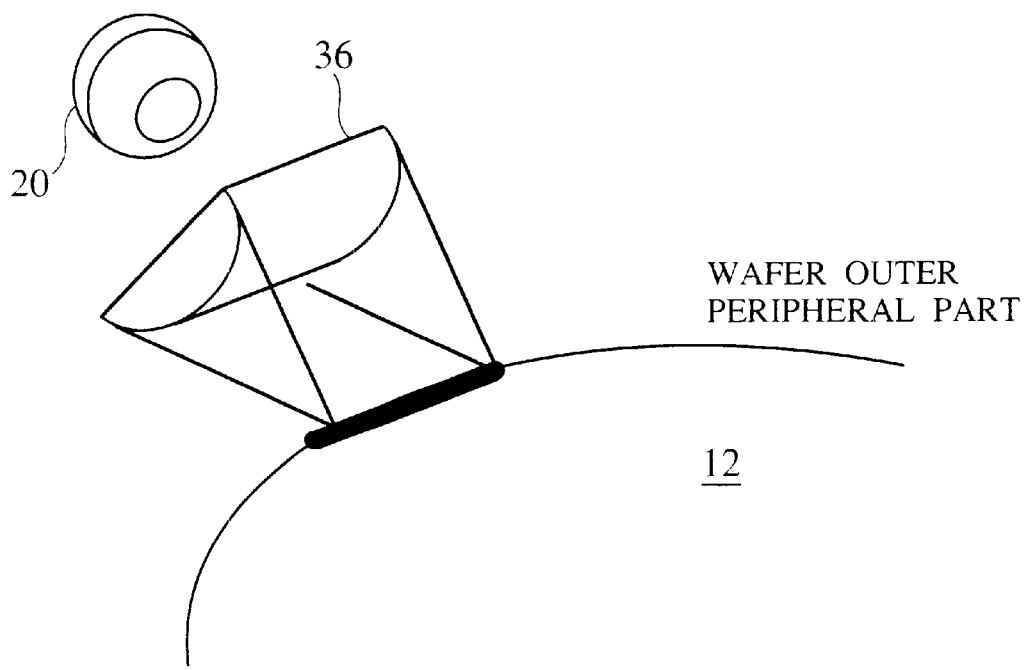
FIGS. 4A and 4B are views explaining a method for condensing by a cylindrical lens or a slit infrared radiation along the wafer outer peripheral part.
Figure 4B:
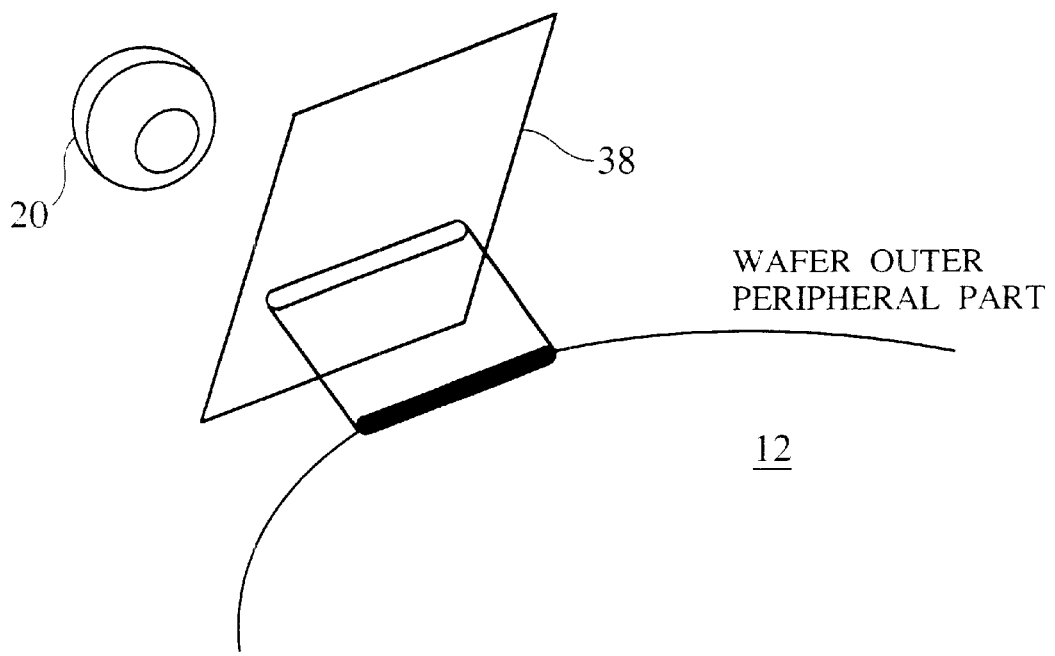
Figure 5:
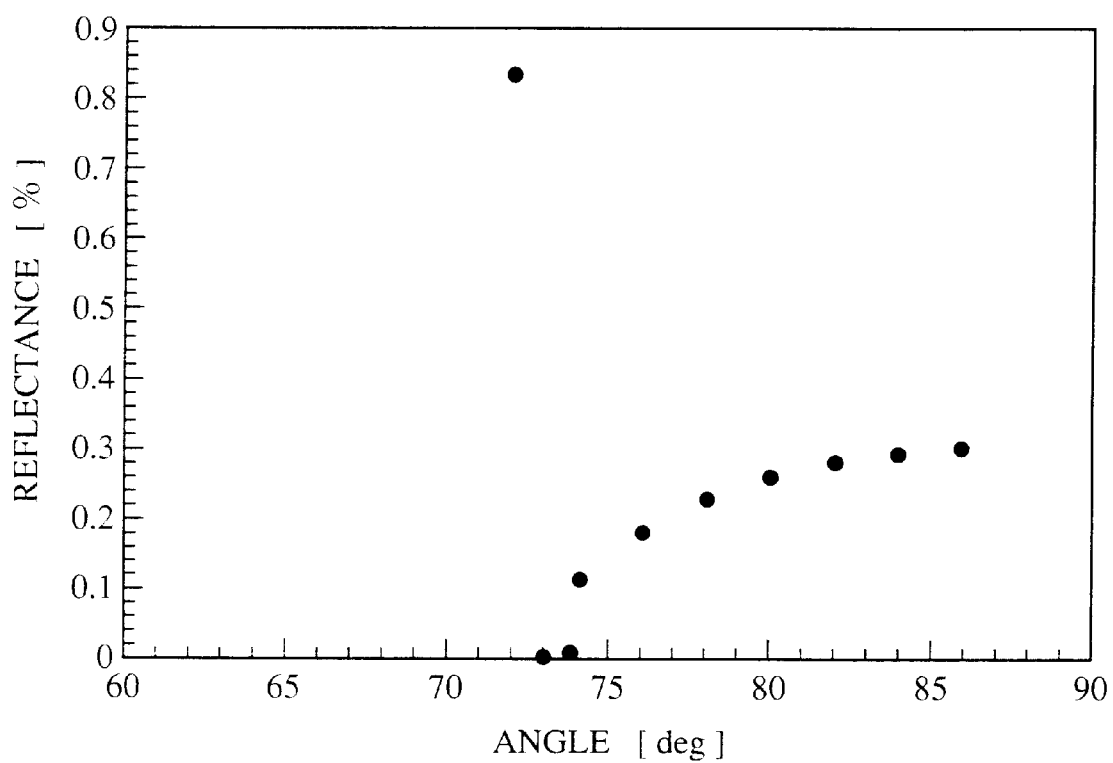
FIG. 5 is a graph of incidence angle dependency of energy reflectance at the time when infrared radiation exit from the inside of a silicon wafer into the air.
Figure 6:
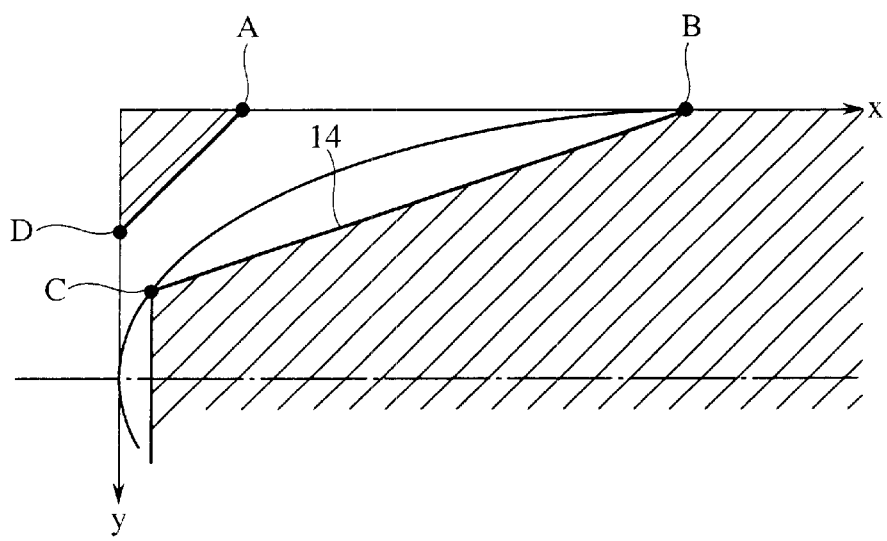
FIG. 6 is a view of shape of the periphery of a 300 mm-wafer in accordance with SEMI standard specifications.
Figure 7:
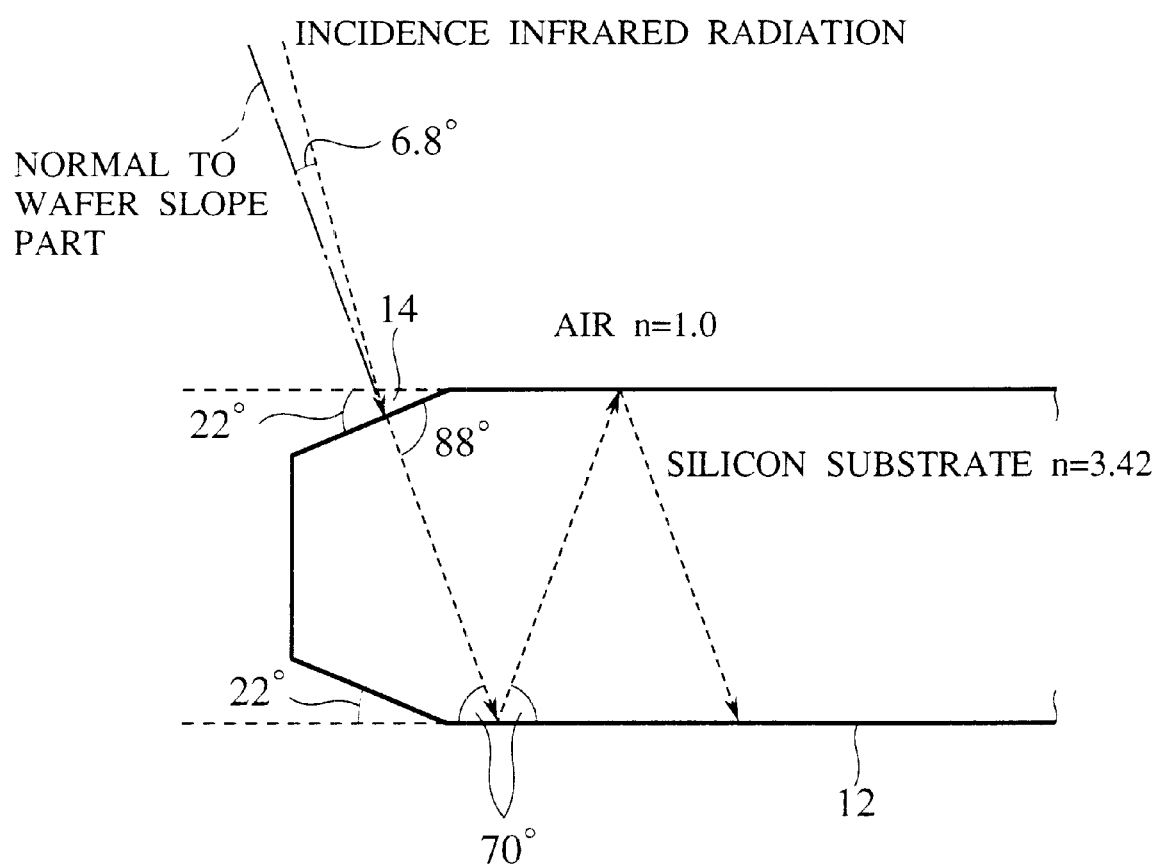
FIG. 7 is a view explaining a method for setting an incidence angle of infrared radiation incident on a wafer-to-be-monitored, which is used in the surface state monitoring method and apparatus according to the first embodiment of the present invention.

FIG. 1 is a diagrammatic view of the surface state monitoring apparatus according to the present embodiment. FIG. 2 is a diagrammatic sectional view of an infrared radiation source of the surface state monitoring apparatus according to the present embodiment. FIGS. 3A and 3B are views explaining a method for condensing infrared radiation by a concave mirror along the wafer outer peripheral part. FIGS. 4A and 4B are views explaining a method for condensing infrared radiation by a cylindrical lens or a slit along the wafer outer peripheral part. FIG. 5 is a graph of incidence angle dependency of energy reflectance at the time when infrared radiation exit from the inside of a silicon wafer into the air. FIG. 6 is a view of a shape of the periphery of a 300 mm-wafer in accordance with SEMI standard specifications. FIG. 7 is a view explaining a method for setting an incident angle of infrared radiation on a wafer-to-be-monitored, which is used in the surface state monitoring method and apparatus according to the present embodiment.

(1) General Structure of the Apparatus

The surface state monitoring apparatus according to the present embodiment will be explained with reference to FIG. 1.

A plurality of semiconductor wafers 12 which are objects to be monitored are held in a wafer cassette 10. An incidence optical system 30 which applies infrared radiation to the semiconductor wafers 12 in the wafer cassette 10, and a detection optical system 40 which detects the infrared radiation which has been transmitted by the semiconductor wafers 12 are disposed on opposed peripheral parts of the wafer cassette 10. As exemplified in FIG. 1, the incidence optical system 30 comprises an infrared radiation source 20 emitting infrared radiation, and two reflection mirrors 32, 34 arranged so that infrared radiation emitted by the infrared radiation source is incident on a semiconductor wafer at a prescribed angle, and converges the infrared radiation emitted by the infrared radiation source 20 to a peripheral part of the semiconductor wafer 12. As exemplified in FIG. 1, the detection optical system 40 comprises two reflection mirrors 42, 44, and converges and guides infrared radiation exited from a semiconductor wafer to an optical spectrum analyzer 50.

Infrared radiation exited from the semiconductor wafer 12 is guided to the optical spectrum analyzer 50 through the detection optical system 40. The optical spectrum analyzer 50 analyzes the infrared radiation transmitted by the semiconductor wafer 12 and detected, and, based on an analysis result, surface states of the semiconductor wafer 12 are analyzed. The optical spectrum analyzer 50 is connected to data storage means 60, and can store analyzed results and can refer to stored databases for the surface analysis of the semiconductor wafer 12.

The wafer cassette 10 is mounted on a movable stage 16 which is vertically displaceable, and can be displaced relatively to the incidence optical system and the detection optical system. Thus, infrared radiation can be incident sequentially on all the semiconductor wafers 12 held in the wafer cassette 10, whereby surface states of the semiconductor wafers 12 can be analyzed, based on results of spectrum analysis of the transmitted infrared radiation. The movable stage 16 is connected to the optical spectrum analyzer 50 through an analysis operation synchronization signal generator 52 and a position signal generator 18, whereby the spectrum analysis can be conducted in synchronization with a timing that the wafer cassette 10 is located at a position where infrared radiation emitted by the incidence optical system 30 can be incident on one of the semiconductor wafers 12 in the wafer cassette 10.

As described above, the surface state monitoring apparatus according to the present embodiment is characterized in that a position of the wafer cassette 10 relative to the incidence optical system 30 and the detection optical system 40 can be replaced so that surface states of a plurality of semiconductor wafers 12 held in the wafer cassette 10 can be continuously monitored. The surface state monitoring apparatus has the above-described structure, whereby a plurality of semiconductor wafers of a cassette unit or a rot unit can be continuously monitored, and when even one of said plurality of wafers has surface abnormality, the unit is monitored to be defective. By using a Fourier infrared optical spectrum analyzer as the optical spectrum analyzer, surface states of a plurality of semiconductor wafers can be monitored, without being additionally machined, in situ on their fabrication line, and the realtime monitoring enables said plurality of semiconductor wafers to be analyzed for a short period time.

Respective members of the surface state monitoring apparatus according to the present embodiment will be detailed with reference to FIGS. 1, 2, 3A–3B, 4A–4B, and 5–7. About the details of the monitoring unit, reference is made to the specification of Japanese Patent Application No. 95853/1999 which inventors of the present application are joined as a co-inventors. The various monitoring units described in the specification are applicable to the surface state monitoring method and apparatus according to the present embodiment.

(a) Infrared Radiation Source 20 As exemplified in FIG. 2, the infrared radiation source 20 comprises a light source 24 for generating infrared radiation or near infrared radiation, a rear reflecting plate 26 and a front reflecting plate 28.

The light source 24 is provided by infrared radiation or near infrared radiation of, e.g., a 2–25 $\mu$m band corresponding to molecular vibrational frequencies of organic molecules. For example, heat rays emitted by applying current to silicon carbide (SiC) as a filament or a ceramic heater may be used as the light source 24. Such light source has characteristics of emitting infrared radiation or near infrared radiation of a 2–25 $\mu$m band and being usable naked in air without burning. Organic molecules having molecular vibrational frequencies corresponding to the infrared radiation or the near infrared radiation in this band are, e.g., alkyl group, olefin, aromatic, aldehyde, amide, amine, linin, nitrile, sulfur oxide, carbon-oxygen bonds, nitrogen-oxygen bonds, etc.

The rear reflection plate 26 and the front reflection plate 28 function, as the members of the infrared radiation source, to improve efficiency of an effective infrared radiation amount with a constant current applied to. The rear reflection plate 26 and the front reflection plate 28 have the surfaces coated with a material which effectively reflects infrared radiation or near infrared radiation, e.g., aluminum or others.

The rear reflection plate 26 is constituted by a parabolic reflection plate and is disposed so that the infrared radiation source 24 is positioned at a focus of the paraboloid. Thus, infrared radiation emitted by the infrared radiation source 24 is transformed into substantially parallel rays.

The front reflection plate 28 is for prohibiting the generation of stray light unnecessary for the monitoring. The front reflection plate 28 as well as the rear reflection plate 28 is constituted by a parabolic reflection plate. The front reflection plate 28 has an exit window through which exits only infrared radiation necessary for the monitoring. Thus, the front reflection plate 28 prevents emitting infrared radiation unnecessary for the monitoring. In addition, infrared radiation reflected on the front reflection plate 28 is again reflected on the rear reflection plate 26, and some of the reflected infrared radiation is transformed into effective parallel rays, with a result of increase of effective infrared radiation. However, the front reflection plate 28 is not essential.

(b) Incidence Optical System 30

In the surface state monitoring apparatus according to the present embodiment, when a surface state of a semiconductor wafer 12 is monitored, infrared radiation is introduced into a semiconductor wafer 12 at a peripheral part thereof. Accordingly, it is important for improving incidence efficiency of the infrared radiation from the infrared radiation source 20 that the infrared radiation is converged into a prescribed shape to be applied to a semiconductor wafer. A preferable shape into which the infrared radiation is converged is a focus of an ellipse along the wafer outer peripheral part.

To converge infrared radiation into an elliptical focal shape an aberration of a lens system is intentionally used. An elongate focal shape can be formed by utilizing a coma aberration or distortion of a lens system. Here a concave mirror 34 having a larger focal distance in the X direction than that in the Y direction is assumed. An elliptical focal shape can be formed on an outer peripheral part of a semiconductor wafer 12 by disposing the infrared radiation source 20 at the center of the concave mirror 34 (see FIG. 3A). When parallel rays are incident on the concave mirror 34 shown in FIG. 3A, reflected infrared radiation forms a focus in the longer axis (X direction) below the wafer 12, and a focus in the shorter axis (Y direction) can be formed on an outer peripheral part of the wafer (see FIG. 3B).

A focal shape of infrared radiation is preferably elliptical but may be circular. The circular focal shape is a little inferior to an elliptical focal shape in incidence efficiency. The circular focal shape can be formed by, e.g., convex lens.

It is possible that infrared radiation is transformed to an elongate focal shape to be applied to the semiconductor wafer 12. As exemplified in FIG. 4A, infrared radiation emitted by the infrared radiation source 20 may be converged by a cylindrical lens 36 or, as shown in FIG. 4B, may be passed through a slit to be applied to.

(c) Arrangement of the Optical System

In the surface state monitoring apparatus according to the present embodiment, it is necessary to converge infrared radiation at one point on the outer peripheral part of the semiconductor wafer 12, cause the infrared radiation which has entered the wafer to undergo internal multiple reflections, and again converge the infrared radiation which has exited at a point symmetrical to the incident point, so as to be guided to the optical spectrum analyzer 50. To this end, it is important how to cause the infrared radiation to efficiently enter the wafer.

Then, conditions for the multiple reflection of infrared radiation inside a wafer and conditions for causing infrared radiation to enter the wafer from the outside will be explained.

In the surface state monitoring apparatus according to the present embodiment, infrared radiation is caused to undergo multiple reflections inside a semiconductor wafer 12, detect molecular vibrations of organic contaminants or chemical contaminants, based on light exuded on the surfaces of the wafer to monitor surface states of the wafer. Accordingly, it is necessary that an incident angle of infrared radiation which enters a semiconductor wafer 12 is set so that the infrared radiation undergoes multiple reflections inside the wafer.

Conditions for infrared radiation undergoes perfect reflection in a wafer are given by computing Snell's law and energy reflectance. In a case that a semiconductor wafer 12 is a silicon substrate, infrared radiation undergoes perfect reflection when infrared radiation forms an angle of 0 to 72° (see FIG. 5). A trace of infrared radiation having an angle in this range is traced back, and an intersection between the end surface of the semiconductor wafer and the infrared radiation is an incidence point of the infrared radiation on the semiconductor wafer.

The surface state monitoring apparatus according to the present embodiment can in-situ monitor a semiconductor wafer 12 without machining, and uses a processed configuration of an end surface of the wafer for the incidence of infrared radiation.

The configurations of the end surfaces of the semiconductor substrates are determined by SEMI (Semiconductor Equipment and Material International), and specifications of 300 mm silicon wafers which are to be used around 2001 have been provisionally decided. The incidence angle of the infrared radiation will be explained by means of, e.g., a 300 mm silicon wafer.

A 300 mm silicon wafer decided by the SEMI standard specifications is as shown in FIG. 6. That is, the wafer has the corners of the peripheral edge chamfered, and in the finished machined configuration, A-B and C-B form an angle of about 22°. The region which is not hatched is an allowable range for configuration machining.

When it is assumed that an incident angle of infrared radiation propagating in the wafer is 70°, and a trace of the infrared radiation is traced back to set an incident point of the infrared radiation at an intersection of the infrared radiation and an end surface (the declined portion 14 between B and C) of the silicon wafer, as shown in FIG. 7, an angle formed by the declined part 14 and the infrared radiation is about 88°. Accordingly, when the angle is calculated back based on Snell's law with a refractive index of the silicon wafer of 3.42; a refractive index of air of 1.0; and an angle formed by a normal of the declined part 14 and infrared radiation of 20, it is found that infrared radiation is incident at an angle of about 6.8° (about 74.8° to the flat surfaces of the wafer) to the normal of the declined part 14 so that the infrared radiation entering the silicon wafer undergo multiple reflections. At this time, an energy reflectance at the incident point is as high as about 29.42%, but infrared radiation is applied in a radiation amount which compensate the high reflectance.

An incident angle of infrared radiation incident on the declined part 14 can be decided by thus calculating back the incident angle, based on an angle of multiple reflections in the wafer.

In cases of semiconductor wafers other than silicon wafers and of end surface configurations different from the described above, incident angles of infrared radiation can be set by the same procedure. Infrared radiation may be incident on the declined part 14 of the front surface of a wafer or the declined part 14 of the back surface of a substrate. Infrared radiation may be incident simultaneously on both the declined parts of the front and the back surfaces.

Other methods for introducing infrared radiation into a wafer are detailed in the specification of Japanese Patent Application No. 95853/1999.

(d) Detection Optical System 40

Infrared radiation incident on a semiconductor wafer 12 exits at a position symmetrical with an incidence position. The detection optical system converges infrared radiation exited from a semiconductor wafer 12 and guides the infrared radiation to the optical spectrum analyzer 50.

The detection optical system 40 comprises, e.g., a concave mirror and a reflection plate. Infrared radiation is converged by the concave mirror and then is guided to the infrared radiation detector 42 through the reflection plate. A convex lens is used in place of the concave mirror, and infrared radiation is passed through the convex lens to be converged.

(e) Optical Spectrum Analyzer 50

Infrared radiation exited from a semiconductor wafer 12 is guided to the optical spectrum analyzer 50 through the detection optical system 40. The optical spectrum analyzer 50 is, e.g., an FT-IR apparatus. Outputs of the optical spectrum analyzer 50 can be given in absorption spectra corresponding to respective frequencies by the mechanism of Fourier transformation spectroscopy by using a two-light flux interferometer.

As described in the basic principle of applying infrared radiation to a semiconductor wafer 12 to cause the infrared radiation to undergo multiple reflections inside the wafer, when the frequency of an evanescent wave oozing when the infrared radiation reflects on the surface of the substrate agrees with the molecular vibrational frequency of the organic contaminants on the substrate surface, the specific frequency component of the infrared radiation is resonance-absorbed. Thus, kinds and amounts of the organic contaminants can be determined by measuring the spectra of the infrared radiation. Kinds and calibration curves of organic contaminants are stored as a database in the data storage means connected to the optical spectrum analyzer. With reference to the data, monitored data are quantitized. Monitored data are stored separately for analysis data of respective semiconductor wafers.

The optical spectrum analyzer may be provided by an infrared spectroscope using a diffraction grating in place of the FT-IR apparatus.

(f) Movable Stage 16

The movable stage 16 changes a positional relationship of the wafer cassette 10 relative to the infrared radiation optical systems 30, 40 so that infrared radiation can be applied to all the semiconductor wafers 12 in the wafer cassette 10.

As described above, when infrared radiation is applied to a semiconductor wafer 12 at a prescribed incidence angle, the infrared radiation enters the semiconductor wafer 12 and undergoes multiple reflections and exits from the semiconductor wafer 12.

Semiconductor wafers 12 are held parallel with each other in the wafer cassette 10. Accordingly, when infrared radiation and one of the semiconductor wafers 12 held in the wafer cassette 10 have a positional relationships with each other which satisfies the above-described conditions, the rest of the semiconductor wafers 12 have the positional relationship with the infrared radiation, which satisfies the above-described conditions when the wafer cassette 10 is displaced vertically to the surfaces of said one of the semiconductor wafers 12.

Accordingly, with the infrared radiation optical. systems being fixed, the wafer cassette 10 is gradually displaced vertically to the surfaces of the semiconductor wafer 12, whereby surface states of all the semiconductor wafers 12 held in the wafer cassette 10 can be sequentially analyzed.

In the present embodiment, Fourier transformation infrared spectrum analysis is applied to surface analysis of semiconductor wafers 12. The analysis method is very effective in cases, such as the present embodiment, where the wafer cassette 10 is moved relative to the infrared radiation optical systems 30, 40. That is, Fourier transformation infrared spectrum analysis can make realtime monitor and accordingly in a short period of time. Accordingly, the wafer cassette 10 is displaceable relative to the infrared radiation optical systems 30, 40, which causes no trouble to the analysis of surface states. In the surface state monitoring method according to the present embodiment, infrared radiation is converged on the peripheral edge of a semiconductor wafer 12 to introduce the infrared radiation into the semiconductor wafer 12, which secures the propagation optical path of the infrared radiation in a plurality of semiconductor wafers 12 kept held in the wafer cassette 10.

The movable stage 16 may be continuously moved or moved discontinuously to a position where infrared radiation is incident on each of the semiconductor wafers 12 in the wafer cassette 10 at a prescribed incidence angle. It is preferable that a mode of moving the movable stage 16 is selected suitably in accordance with required monitoring sensitivity and monitoring time.

Figure 8:
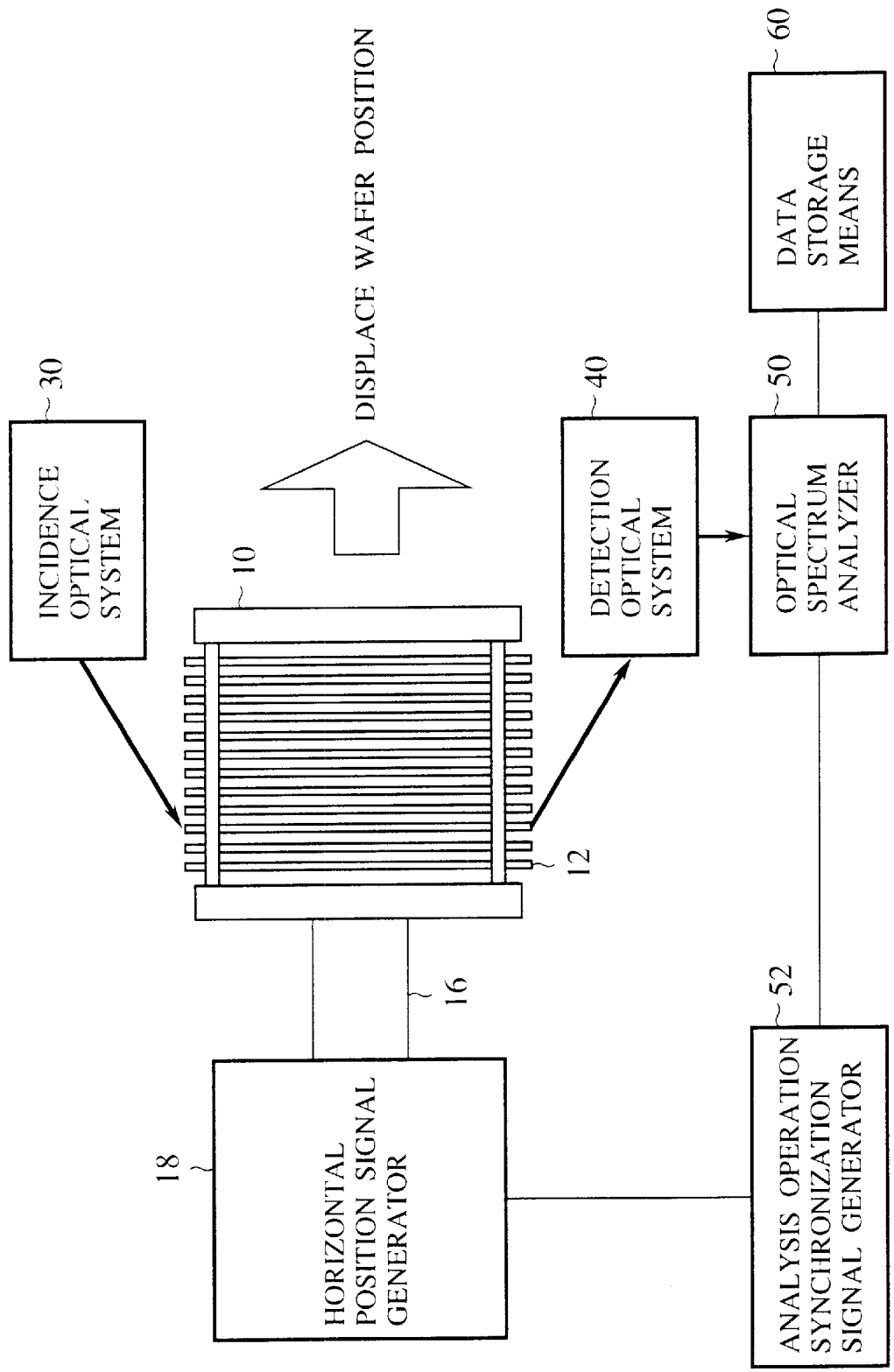
FIG. 8 is a diagrammatic view of the surface monitoring apparatus according to one modification of the first embodiment.

In the surface state monitoring apparatus shown in FIG. 1, the wafer cassette 10 is arranged to be vertically displaced but may be arranged to be displaced horizontally as exemplified in FIG. 8.

The surface state monitoring apparatus shown in FIG. 1 comprises an analysis operation synchronization signal generator 52 and the position signal generator 18, whereby the movement of the movable stage 16 and the analysis of the optical spectrum analyzer 50 are synchronized. However, it is not essential to synchronize the movement of the movable state 16 and the analysis of the optical spectrum analyzer 50 with each other.

In the surface state monitoring apparatus according to the present embodiment, the wafer cassette 10 is mounted on the movable stage 16, whereby the wafer cassette 10 can be displaced relative to the incidence optical system 30 and the detection optical system 40. However, it is possible that the incidence optical system 30 and the detection optical system 40 are displaceable. It is also possible that both the wafer cassette 10, and the incidence optical system 30 and the detection optical system 40 are displaceable.

(2) Surface State Monitoring Method

The surface state monitoring method according to the present embodiment will be explained with reference to FIG. 1.

First, semiconductor wafers 12 to be monitored are held in the wafer cassette 10. Twenty five, for example, of 300 mm silicon wafers are held one wafer cassette. The wafer cassette 10 can be a wafer cassette to be used in a semiconductor device fabrication line.

Then, the wafer cassette 10 holding the semiconductor wafers 12 is mounted on the movable state 16 of the surface state monitoring apparatus according to the present embodiment.

Next, the infrared radiation optical systems 30, 40 are positioned. The infrared radiation optical systems 30, 40 are positioned optimumly, so that infrared radiation converged by the incident optical system 30 is incident at a prescribed angle on the declined part 14 of one semiconductor wafer 12, and the infrared radiation undergoes multiple reflections inside the semiconductor wafer 12 to be detected in a maximum radiation amount by the detection optical system 40.

Then, the semiconductor wafer 12 is positioned with respect to an infrared radiation path. The semiconductor wafer 12 is positioned by the movable state 16 operated by the position signal generator 18 to displace the wafer cassette 10 so that infrared radiation emitted by the incidence optical system 30 is applied to the declined part 14 of the semiconductor wafer 12.

Then, in response to the detection, by the detection optical system 40, of infrared radiation transmitted by the semiconductor wafer 12 or the detection of a position signal of the semiconductor wafer 12, the position signal generator 18 supplies to the analysis operation synchronization signal generator 52 a signal indicating the finish of the positioning of the semiconductor wafer 12.

Next, the analysis operation synchronization signal generator 52, which has received the signal of the finish of the positioning, supplies a signal of start of the spectroscopy to the optical spectrum analyzer 50, and the optical spectrum analyzer 50 starts spectrum analysis.

When the optical spectrum analyzer 50 starts the spectrum analysis, the optical spectrum analyzer 50 analyzes infrared radiation which has passed through the semiconductor wafer 12, probing a surface state of the semiconductor wafer 12 and detected by the detection optical system 40, and identify contaminants staying on the surfaces of the semiconductor wafer 12 or computes amounts of the contaminants. Analyzed data are stored in the data storage means 60 for each semiconductor wafer. Thus, the analysis of one of the semiconductor wafers 12 held in the wafer cassette 10 is completed.

Subsequently, by the same method as described above, a next one of the semiconductor wafers 12 held in the wafer cassette 10 is positioned, and the surface analysis is made. This analysis is repeated until all the semiconductor wafers held in the wafer cassette are monitored.

As describe d above, according to the present embodiment, surface states of a plurality of semiconductor wafers held in the wafer cassette are continuously monitored by spectrum analysis by Fourier transformation infrared spectroscopy with a position of the wafer cassette relative to the infrared radiation optical system being displaced, whereby surface states of the semiconductor wafers held in the wafer cassette can be monitored continuously for a short period of time.

The data storage means 60 which stores monitored data for each of wafer is provided, whereby not only each of wafer but also a wafer cassette of wafers can be monitored, which is useful for statistic administration of fabrication yields.

A Second Embodiment

The surface state monitoring method and apparatus according to a second embodiment of the present invention will be explained with reference to FIGS. 9 to 11. The same member s of the present embodiment as those of the surface state monitoring method and apparatus according to the first embodiment are represented by the same reference numbers not to rep eat or to simplify their explanation.

Figure 9:
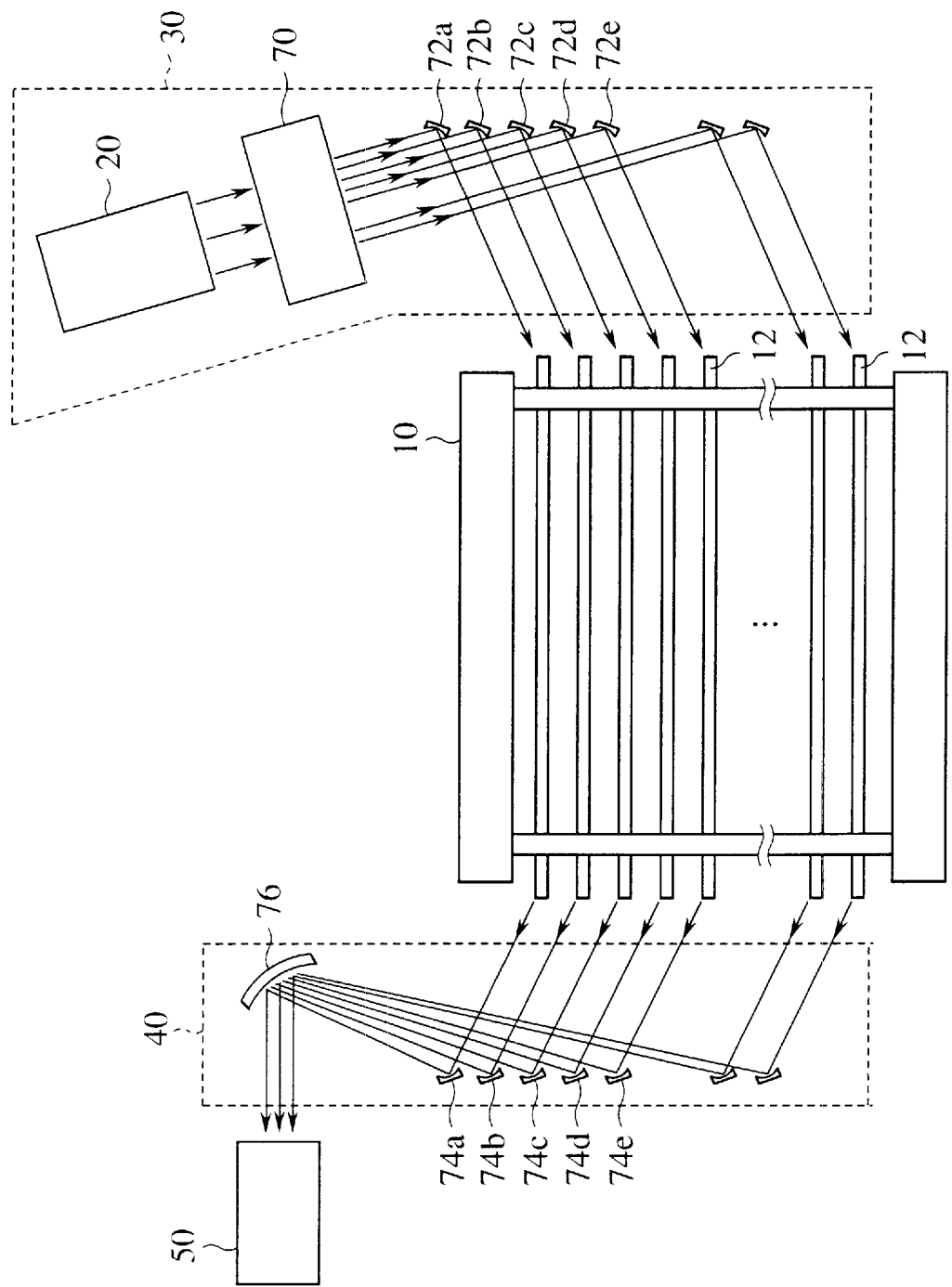
FIG. 9 is a diagrammatic view of the surface state monitoring apparatus according to a second embodiment of the present invention.

FIG. 9 is a diagrammatic view of the surface state monitoring apparatus according to the present embodiment. FIGS. 10 and 11 are views of examples of incident infrared radiation selection means of the surface sate monitoring apparatus according to the present embodiment.

(1) Surface State Monitoring Apparatus

The surface state monitoring apparatus according to the present embodiment will be explained with reference to FIGS. 9 to 11.

A plurality of semiconductor wafers 12 which are objects to be monitored are held in a wafer cassette 10. An incidence optical system 30 which applies infrared radiation to the semiconductor wafers 12 in the wafer cassette 10, and a detection optical system 40 which detects the infrared radiation which has been transmitted by the semiconductor wafers 12 are disposed on opposed peripheral parts of the wafer cassette 10. As exemplified in FIG. 9, the incidence optical system 30 comprises an infrared radiation source 20 emitting infrared radiation, and a plurality of reflection mirrors 72a, 72b, 72c, . . . arranged so that infrared radiation emitted by the infrared radiation source is incident on each semiconductor wafer 12 at a prescribed angle, and incident infrared radiation selecting means 70 which applies infrared radiation from the infrared radiation source 20 selectively to one of said plurality of reflection mirrors 72a, 72b, 72c, . . . , whereby the incidence optical system 30 converges the infrared radiation to a peripheral part 14 of one of the semiconductor wafers 12 held in the wafer cassette 10. As exemplified in FIG. 9, the detection optical system 40 comprises a plurality of reflection mirrors 74a, 74b, 74c, . . . which respectively infrared radiation exiting each semiconductor wafer 12, and a reflection mirror 76 which introduces the infrared radiation reflected by the reflection mirrors 74a, 74b, 74c, . . . to an optical spectrum analyzer 50.

Infrared radiation exited from a semiconductor wafer 12 is guided to the optical spectrum analyzer 50 through the detection optical system 40. The optical spectrum analyzer 50 analyzes the infrared radiation transmitted by the semiconductor wafer 12 and detected, and, based on an analysis result, surface states of the semiconductor wafer 12 are analyzed. The optical spectrum analyzer 50 is connected to data storage means 60, and can store analyzed results and can refer to stored databases for the surface analysis of the semiconductor wafer 12.

As described above, the surface state monitoring apparatus according to the present embodiment is characterized in that an infrared radiation optical path of the incidence optical system 30 is suitably changed to sequentially monitor a plurality of semiconductor wafers 12 held in the wafer cassette 10. The surface state monitoring apparatus according to the present embodiment has such structure, whereby a plurality of semiconductor wafers of a cassette unit or a rot unit can be continuously monitored, and when even one of said plurality of wafers has surface abnormality, the unit is monitored to be defective.

The incident infrared radiation selecting means 70 may include the means exemplified below. However, the incident infrared radiation selecting means 70 is not limited to the following means.

Figure 10:
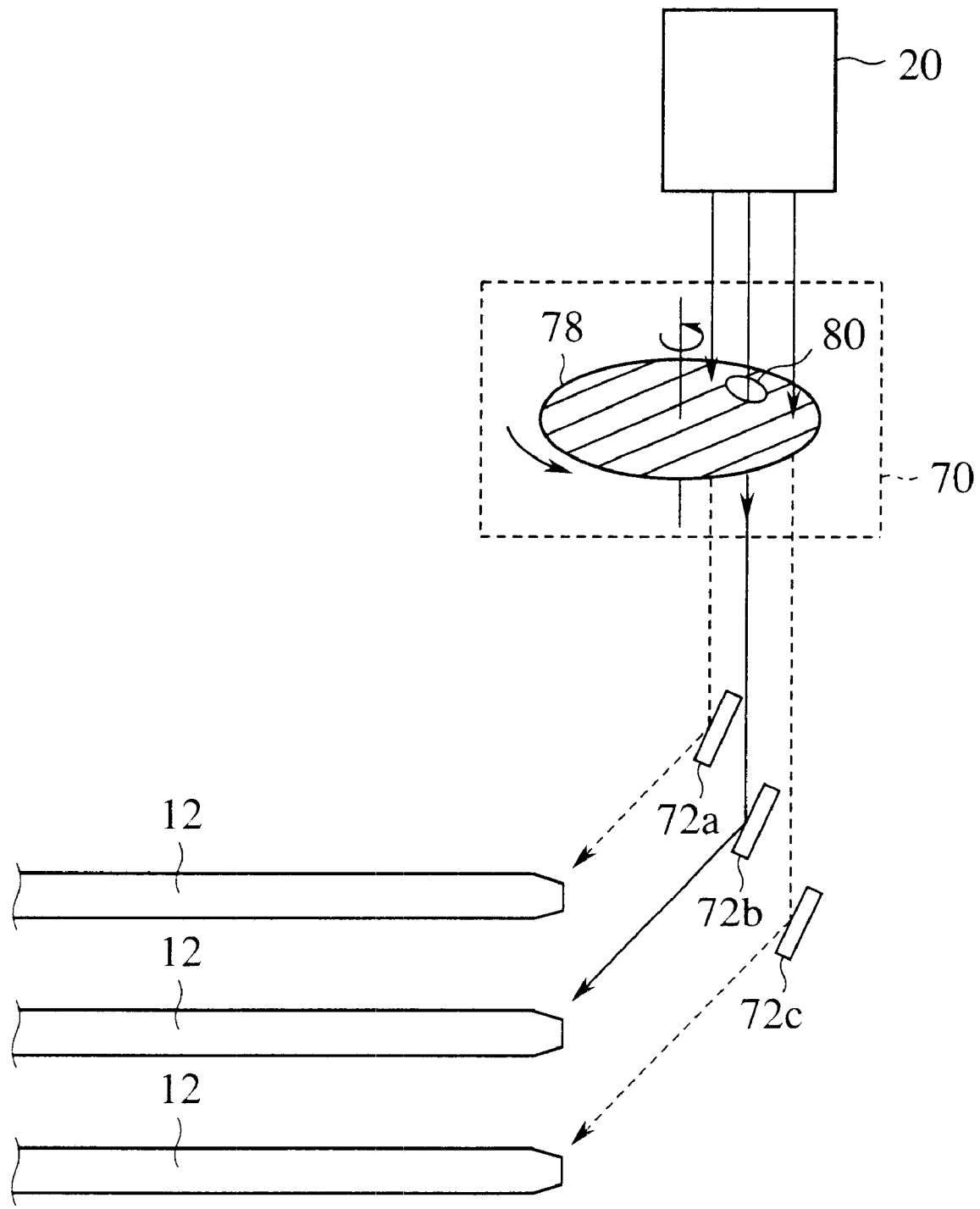
FIG. 10 is a view of incident infrared radiation selecting means of the surface state monitoring apparatus according to the second embodiment of the present invention (Part 1).

As exemplified in FIG. 10, a first example of the incident infrared radiation selecting means 70 includes a rotary shield plate 78 having an aperture 80 formed in a prescribed position which is disposed between the infrared radiation source 20 and the reflection mirrors 72a, 72b, 72c, . . . Infrared radiation emitted by the infrared radiation source 20 can be selectively applied to one (the reflection mirror 72b in the drawing) of the reflection mirrors 72a, 72b, 72c, . . . corresponding to a location of the aperture 80 in the shield plate 78, whereby the infrared radiation from the infrared radiation source 20 can be selectively incident on one of the semiconductor wafers 12 held in the wafer cassette 10. The shield plate 78 is rotated to apply infrared radiation to one of the other reflection mirrors 72a, 72b, 72c, . . . , whereby the infrared radiation can be incident on one of the other semiconductor wafers 12 corresponding to said one of the reflection mirrors.

Figure 11:
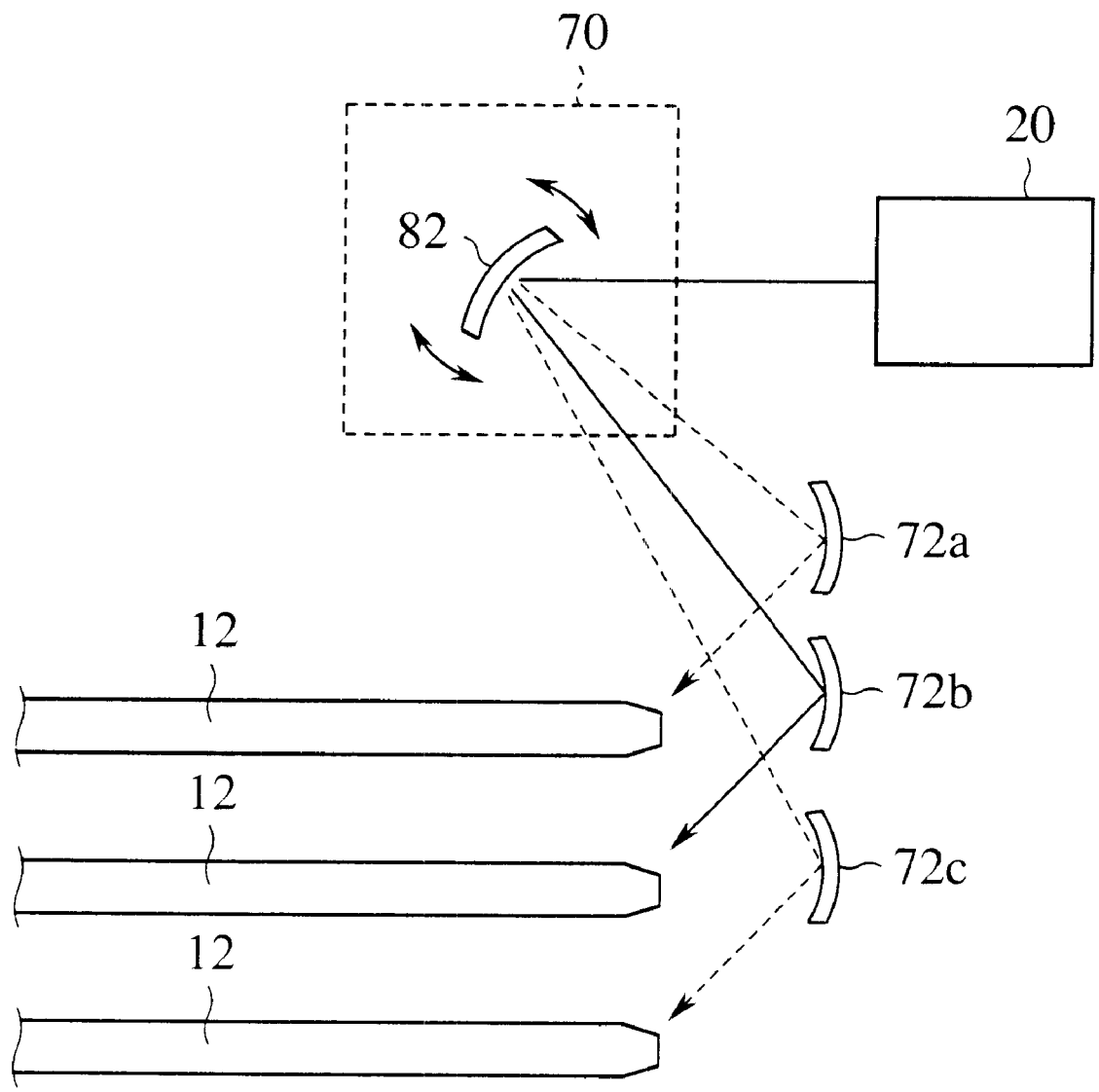
FIG. 11 is a view of incident infrared radiation selecting means of the surface state monitoring apparatus according to the second embodiment of the present invention (Part 2).

As exemplified in FIG. 11, a second example of the incident infrared radiation selecting means 70 includes a variable reflection mirror 82 which is disposed between the infrared radiation source 20 and the reflection mirrors 72a, 72b, 72c, . . . Infrared radiation emitted by the infrared radiation source 20 can be selectively applied to one (the reflection mirror 72b in the drawing) of the reflection mirrors 72a, 72b, 72c, . . . corresponding to an angle of the variable reflection mirror 82, whereby the infrared radiation from the infrared radiation source 20 can be selectively incident on one of the semiconductor wafers 12 held in the wafer cassette 10.

In using these examples of the incident infrared radiation selecting means 70, it is preferable that a rotation frequency of the shield plate 78 or an angle of the variable reflection mirror 82 is synchronized with analysis processing of the optical spectrum analyzer 50 to detect which semiconductor wafer 12 information a detection signal indicates. The surface state monitoring apparatus having such constitution can easily identify a semiconductor wafer 12 having surface abnormalities.

In place of thus providing the incident infrared radiation selecting means 70, the same infrared radiation selecting means 70 may be disposed in the infrared radiation optical path of the detection optical system 40 to selectively guide to the optical spectrum analyzer 50 infrared radiation which has been transmitted by one of the semiconductor wafers 12. The infrared radiation selecting means may have the same structure as that exemplified in FIG. 10 or 11.

(2) Surface State Monitoring Method

The surface state monitoring method according to the present embodiment will be explained below.

First, semiconductor wafers 12 to be monitored are held in the wafer cassette 10. Twenty five, for example, of 300 mm silicon wafers are held one wafer cassette. The wafer cassette 10 can be a wafer cassette to be used in a semiconductor device fabrication line.

Next, the wafer cassette 10 holding the semiconductor wafers 12 is mounted on the surface state monitoring apparatus according to the present embodiment.

Then, the infrared radiation optical system is positioned. In positioning the incidence optical system 30, the respective reflection mirrors 72a, 72b, 72c, . . . have angles adjusted so that infrared radiation emitted by the infrared radiation source 20 is reflected by each of the reflection mirrors 72a, 72b, 72c, . . . to be incident on each of the declined parts 14 of the semiconductor wafers 12 held in the wafer cassette 10, and the infrared radiation detected after the multiple reflection inside the semiconductor wafers 12 can be detected in a maximum radiation amount. In adjusting the detection optical system 40, the reflection mirrors 74a, 74b, 74c, . . . have angles adjusted so that infrared radiation transmitted by each of the semiconductor wafers 12 is reflected by the reflection mirror 76 to be guided to the optical spectrum analyzer 50 after reflected by each of the reflection mirrors 74a, 74b, 74c, . . . .

Next, one of the semiconductor wafers 12 to which infrared radiation from the infrared radiation source 20 is applied by the incident infrared radiation selecting means 70 is selected, and the infrared radiation is applied to the selected semiconductor wafer 12. The optical spectrum analyzer 50 analyzes infrared radiation which has passed through the semiconductor wafer 12, probing surface states of the semiconductor wafer 12 and detected by the detection optical system 40, and identify contaminants staying on the surfaces of the semiconductor wafer 12 or computes amounts of the contaminants. Analyzed data are stored in the data storage means 60 for each semiconductor wafer 12.

Then, a next one of the semiconductor wafers 12 held in the wafer cassette 10 to which infrared radiation is applied is selected by the incident infrared radiation selecting means 70, and the surface analysis is made on the next selected semiconductor wafer 12 by the same procedures. This analysis is repeated until all the semiconductor wafers 12 held in the wafer cassette 10 are monitored.

Thus, the surface analysis is completed on all of a plurality of semiconductor wafers 12 held in the wafer cassette 10.

As described above, according to the present embodiment, surface states of a plurality of semiconductor wafers held in the wafer cassette are continuously monitored by spectrum analysis by Fourier transformation infrared spectroscopy with an optical path of incident infrared radiation changed, whereby surface states of the semiconductor wafers held in the wafer cassette can be monitored continuously for a short period of time.

In the present embodiment, the respective reflection mirrors 72a, 72b, 72c, . . . , and the respective reflection mirrors 74a, 74b, 74c, . . . correspond to respective ones of a plurality of semiconductor wafers 12 held in the wafer cassette 10. However, it is not essential to provide one reflection mirror 72 and one reflection mirror 74 are provided for each of a plurality of semiconductor wafers 12 held in the wafer cassette 10. For example, it is possible that the reflection mirrors 72a, 72b, 72c, . . . , and the reflection mirrors 74a, 74b, 74c, . . . correspond to a part of a plurality of semiconductor wafers 12 held in the wafer cassette 10, and furthermore, the movable stage for displacing the wafer cassette 10 is provided as in the surface state monitoring apparatus according to the first embodiment, whereby the surface state monitor according to the present embodiment, and the same displacement of the wafer cassette 10 as in the first embodiment are repeated to analyze all of said plurality of semiconductor wafers 12 held in the wafer cassette 10.

In the present embodiment, infrared radiation to be applied to all of a plurality of semiconductor wafers is supplied by one infrared radiation source. However, it is possible that one infrared radiation source is provided for a unit of one semiconductor wafer, or two or more semiconductor wafers.

It is possible that individual infrared radiation optical systems are provided for a plurality of semiconductor wafers held in the wafer cassette, whereby said plurality of semiconductor wafers are simultaneously or continuously analyzed.

A Third Embodiment

The surface state monitoring method and apparatus according to a third embodiment of the present invention will be explained with reference to FIG. 12. The same members of the present embodiment as those of the surface state monitoring method and apparatus according to the first and the second embodiments are represented by the same-reference numbers not to repeat or to simplify their explanation.

Figure 12:
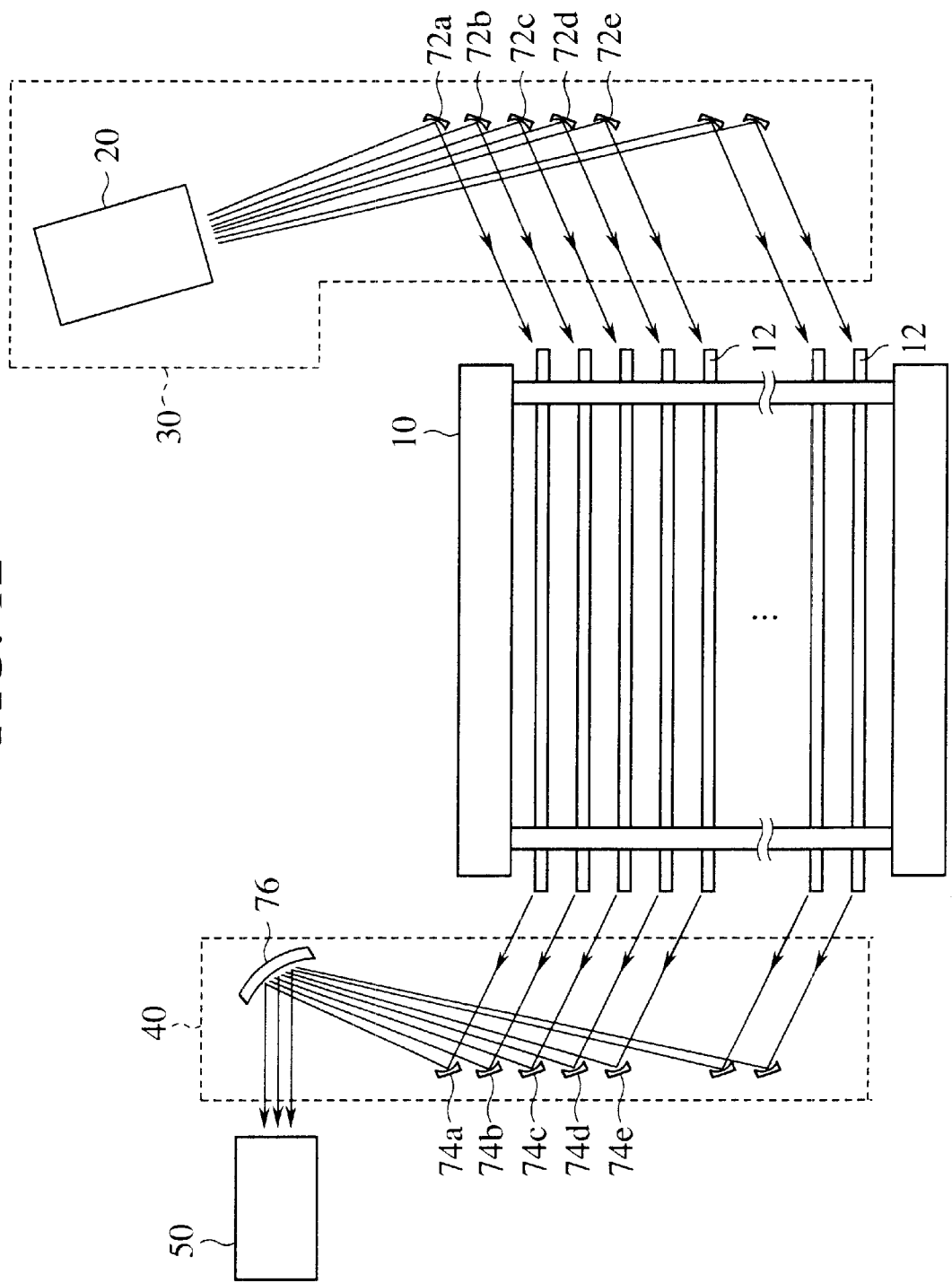
FIG. 12 is a diagrammatic view of the surface state monitoring apparatus according to a third embodiment of the present invention.
Figure 13A:
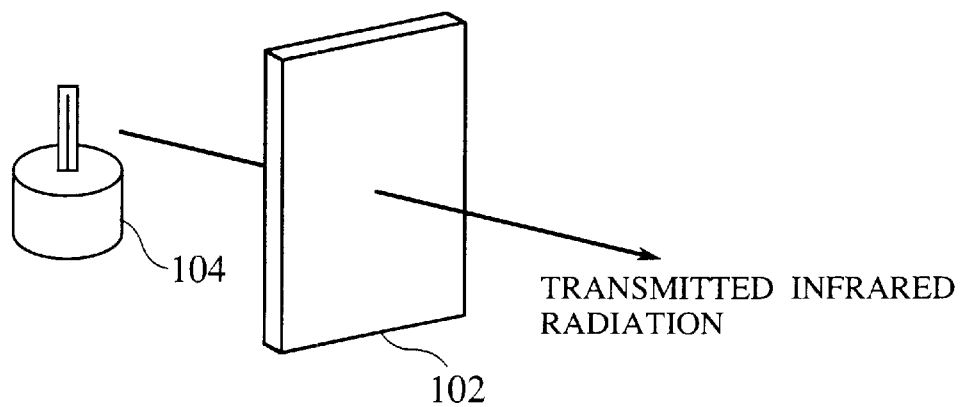
FIGS. 13A–13C are diagrammatic views explaining the conventional surface state monitoring methods and apparatuses.
Figure 13B:
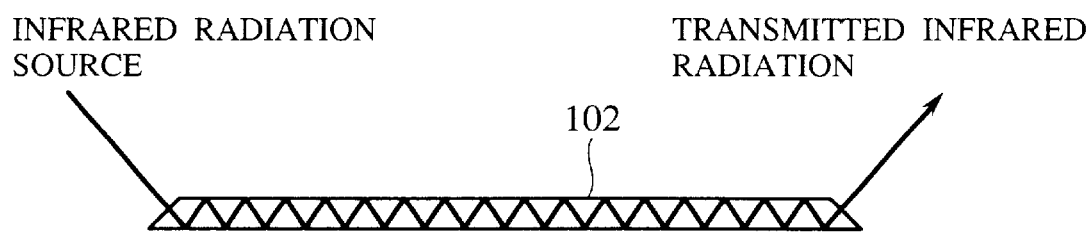
Figure 13C:
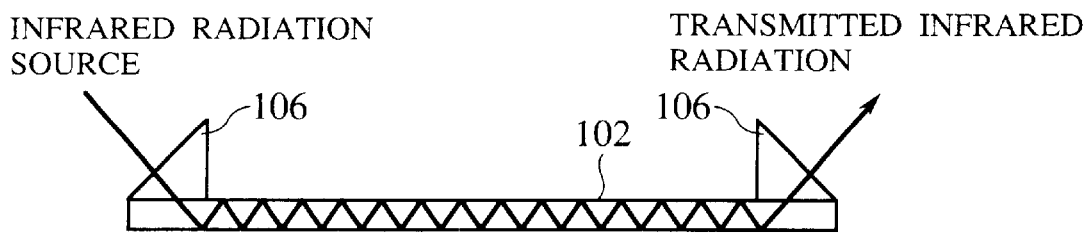

FIG. 12 is a diagrammatic view of the surface state monitoring apparatus according to the present embodiment.
(1) Surface State Monitoring Apparatus The surface state monitoring apparatus according to the present embodiment will be explained with reference to FIG. 12.

A plurality of semiconductor wafers 12 which are objects to be monitored are held in a wafer cassette 10. An incidence optical system 30 which applies infrared radiation to the semiconductor wafers 12 in the wafer cassette 10, and a detection optical system 40 which detects the infrared radiation which has been transmitted by the semiconductor wafers 12 are disposed on opposed peripheral parts of the wafer cassette 10. As exemplified in FIG. 12, the incidence optical system 30 comprises an infrared radiation source 20 emitting infrared radiation, and a plurality of reflection mirrors 72a, 72b, 72c, . . . arranged so that infrared radiation emitted by the infrared radiation source 20 is incident on the respective semiconductor wafers 12 at a prescribed angle, whereby infrared radiation emitted by the infrared radiation source 20 is converged simultaneously at peripheral parts of the respective semiconductor wafers 12. As exemplified in FIG. 12, the detection optical system 40 comprises a plurality of reflection mirrors 74a, 74b, 74c, . . . which respectively infrared radiation exited from each semiconductor wafer 12, and a reflection mirror 76 which introduces the infrared radiation reflected by the reflection mirrors 74a, 74b, 74c, . . . to an optical spectrum analyzer 50.

Infrared radiation exited from the semiconductor wafers 12 is guided to the optical spectrum analyzer 50 through the detection optical system 40. The infrared radiation which has been transmitted by the semiconductor wafers 12 and detected is analyzed by the optical spectrum analyzer 50, and based on analysis results, surface states of the semiconductor wafers 12 can be analyzed. The optical spectrum analyzer 50 is connected to data storage means 60 (not shown), and can store analyzed results and can refer to stored databases for the surface analysis of the semiconductor wafer 12.

As described above, the surface state monitoring apparatus according to the present embodiment is characterized in that a plurality of semiconductors can have surface states simultaneously monitored. When surface abnormalities are present on the surface of at least one of a plurality of semiconductor wafers held in the wafer cassette 10, the surface abnormalities can be detected by the surface state monitoring apparatus having such constitution.

The surface state monitoring apparatus according to the present embodiment cannot identify one of a-plurality of semiconductor wafers held in the wafer cassette having surface abnormalities, as can be in the surface state monitoring apparatus according to the first and the second embodiment. However, the present embodiment does not require the movable stage of the surface state monitoring apparatus according to the first embodiment and the incident infrared radiation selecting means of the surface state monitoring apparatus according to the second embodiment. The surface state monitoring apparatus according to the present embodiment can have a simple constitution. Furthermore, a plurality of semiconductor wafers 12 held in the wafer cassette 10 are simultaneously monitored, which results in a much shorter analyzing period of time.
(2) Surface State Monitoring Method The surface state monitoring method according to the present embodiment will be explained below.

First, semiconductor wafers 12 to be monitored are held in the wafer cassette 10. Twenty five, for example, of 300 mm silicon wafers are held one wafer cassette. The wafer cassette 10 can be a wafer cassette to be used in a semiconductor device fabrication line.

Next, the wafer cassette 10 holding the semiconductor wafers 12 is mounted on the surface state monitoring apparatus according to the present embodiment.

Then, the infrared radiation optical system is positioned. In positioning the incidence optical system 30, the respective reflection mirrors 72a, 72b, 72c, . . . have angles adjusted so that infrared radiation emitted by the infrared radiation source 20 is reflected by all the reflection mirrors 72a, 72b, 72c, . . . to be incident on the declined parts 14 of all of said plurality of semiconductor wafers 12 held in the wafer cassette 10, and the infrared radiation is detected after the multiple reflection inside the respective semiconductor wafers 12 can be detected in maximum radiation amounts. In adjusting the detection optical system 40, the reflection mirrors 74a, 74b, 74c, . . . have angles adjusted so that infrared radiation transmitted by the respective semiconductor wafers 12 is reflected by the reflection mirror 76 to be guided to the optical spectrum analyzer 50 after reflected by the respective reflection mirrors 74a, 74b, 74c, . . . .

The optical spectrum analyzer 50 analyzes collectively infrared radiation which has passed through the semiconductor wafers 12, proving surface states and detected by the detection optical system to thereby identify contaminants staying on the surfaces of the semiconductor wafers or computes amounts of the staying contaminants. Analyzed data are stored for each wafer cassette in data storage means 60. Thus, the analysis of said plurality of semiconductor wafers held in the wafer cassette is completed.

Ethyl alcohol, which is a typical organic contamination source for contaminating surfaces of wafers, was applied to the surface of an arbitrary 300 mm silicon wafer, and the analysis was made on 25 silicon wafers held in the wafer cassette by the surface state monitoring method according to the present embodiment. Ethyl alcohol was identified by absorption spectra. Water was applied to other wafers, and the same analysis was made on the wafers. Absorption of infrared radiation by ethyl alcohol and water was confirmed.

As described above, according to the present embodiment, surface states of a plurality of semiconductor wafers held in the wafer cassette are collectively monitored by spectrum analysis by Fourier transformation infrared spectroscopy, whereby it can be analyzed in a very short time whether or not surface abnormalities are present on any one of the semiconductor wafers held in the wafer cassette.

In the present embodiment, the respective reflection mirrors 72a, 72b, 72c, . . . , and the respective reflection mirrors 74a, 74b, 74c, . . . correspond to respective ones of a plurality of semiconductor wafers 12 held in the wafer cassette 10. However, it is not essential to provide one reflection mirror 72 and one reflection mirror 74 are provided for each of a plurality of semiconductor wafers 12 held in the wafer cassette 10. For example, it is possible that the reflection mirrors 72a, 72b, 72c, . . . , and the reflection mirrors 74a, 74b, 74c, . . . correspond to a part of a plurality of semiconductor wafers 12 held in the wafer cassette 10, and furthermore, the movable stage for displacing the wafer cassette 10 is provided as in the surface state monitoring apparatus according to the first embodiment, whereby the surface state monitor according to the present embodiment, and the same displacement of the wafer cassette 10 as in the first embodiment are repeated to analyze all of said plurality of semiconductor wafers 12 held in the wafer cassette 10.

In the present embodiment, infrared radiation is applied simultaneously to all of a plurality of semiconductor wafers held in the wafer cassette by one infrared radiation source. However, it is possible that one infrared radiation source is provided for each unit of one semiconductor wafer, or two or more semiconductor wafers.

What is claimed is:

1. A surface state monitoring apparatus comprising:

a wafer cassette holding a plurality of semiconductor wafers;

an incidence optical system for applying infrared radiation to at least one of said plurality of semiconductor wafers;

a detection optical system for detecting infrared radiation which has undergone multiple reflection in the semiconductor wafer and exited from the semiconductor wafer;

surface state monitoring means for monitoring surface states of the semiconductor wafer, based on the infrared radiation detected by the detection optical system; and displacing means for displacing the wafer cassette relative to the incidence optical system and the detection optical system, surface states of said plurality of semiconductor wafers being sequentially monitored while the wafer cassette is displaced relative to the incidence optical system and the detection optical system by the displacing means, whereby surface states of said plurality of semiconductor wafers held in the wafer cassette are continuously monitored.

2. A surface state monitoring apparatus comprising:

a wafer cassette holding a plurality of semiconductor wafers;

an incidence optical system for applying infrared radiation to at least one of said plurality of semiconductor wafers;

a detection optical system for detecting infrared radiation which has undergone multiple reflection in the semiconductor wafer and exited from the semiconductor wafer; and surface state monitoring means for monitoring surface states of the semiconductor wafer, based on the infrared radiation detected by the detection optical system, the incidence optical system being controlled to apply the infrared radiation sequentially to said semiconductor wafers, whereby surface states of said plurality of semiconductor wafers held in the wafer cassette being continuously monitored.

3. A surface state monitoring apparatus comprising:

a wafer cassette holding a plurality of semiconductor wafers;

an incidence optical system for applying infrared radiation to at least two or more of said semiconductor wafers;

a detection optical system for collectively detecting infrared radiations which have undergone multiple reflection in the semiconductor wafers and exited from the semiconductor wafers, respectively; and surface state monitoring means for monitoring surface states of the semiconductor wafers, based on the infrared radiations detected by the detection optical system.

4. A surface state monitoring apparatus according to claim 2, further comprising:

displacing means for displacing the wafer cassette relative to the incidence optical system and the detection optical system.

5. A surface state monitoring apparatus according to claim 3, further comprising:

displacing means for displacing the wafer cassette relative to the incidence optical system and the detection optical system.

6. A surface state monitoring method comprising: applying infrared radiation to at least one of a plurality of semiconductor wafers held in a wafer cassette, detecting infrared radiation which has undergone multiple reflection in the semiconductor wafer and exited from the semiconductor wafer, and analyzing the detected infrared radiation to monitor surface states of the semiconductor wafer, surface states of the semiconductor wafer being monitored while the wafer cassette is displaced relative to an infrared radiation optical system to continuously monitor surface states of said plurality of semiconductor wafers held in the wafer cassette.

7. A surface state monitoring method according to claim 6, wherein the wafer cassette is intermittent displaced wafer by wafer relative to the infrared radiation optical system.

8. A surface state monitoring method according to claim 6, wherein the wafer cassette is continuously displaced relative to the infrared radiation optical system.

9. A surface state monitoring method according to claim 8, wherein a displacement of the wafer cassette relative to the infrared radiation optical system, and a monitor of surface states of the semiconductor wafer are synchronized with each other.

10. A surface state monitoring method according to claim 6, wherein a displacement of the wafer cassette relative to the infrared radiation optical system, and a monitor of surface states of the semiconductor wafer are synchronized with each other.

11. A surface state monitoring method according to claim 7, wherein a displacement of the wafer cassette relative to the infrared radiation optical system, and a monitor of surface states of the semiconductor wafer are synchronized with each other.

12. A surface state monitoring method comprising: applying infrared radiation to at least one of a plurality of semiconductor wafers held in a wafer cassette, detecting infrared radiation which has undergone multiple reflection in the semiconductor wafer and exited from the semiconductor wafer, and analyzing the detected infrared radiation to monitor surface states of the semiconductor wafer, an infrared radiation optical system being controlled to apply infrared radiation sequentially to a different one of said plurality of semiconductor wafers, whereby surface states of said plurality of semiconductor wafers held in the wafer cassette are continuously monitored.

13. A surface state monitoring method according to claim 12, wherein a control of the infrared radiation optical system and a monitor of surface states of the semiconductor wafer are synchronized with each other.

14. A surface state monitoring method comprising:

applying infrared radiation to respective at least two or more of a plurality of semiconductor wafers held in a wafer cassette;

collectively detecting infrared radiations which has undergone multiple reflection in the semiconductor wafers and exited from the semiconductor wafers, respectively; and analyzing the detected infrared radiation to monitor surface states of the semiconductor wafers.

15. A surface state monitoring method according to claim 14, wherein surface states of said plurality of semiconductor wafers held in the wafer cassette are collectively monitored.

* * * * *